US011936426B2

(12) United States Patent
Burdin et al.

(10) Patent No.: US 11,936,426 B2
(45) Date of Patent: *Mar. 19, 2024

(54) OPTICAL TRANSMISSION FOR AN IMPLANTABLE SYSTEM

(71) Applicant: Wyss Center for Bio and Neuro Engineering, Geneva (CH)

(72) Inventors: Florent Burdin, Gland (CH); Tiago Bertolote, Le Grand-Saconnex (CH); Olivier Coquoz, Geneva (CH)

(73) Assignee: Wyss Center for Bio and Neuro Engineering, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,677

(22) Filed: Feb. 3, 2023

(65) Prior Publication Data
US 2023/0239048 A1     Jul. 27, 2023

Related U.S. Application Data

(63) Continuation of application No. 17/765,312, filed as application No. PCT/IB2020/059735 on Oct. 15, 2020, now Pat. No. 11,575,434.
(Continued)

(51) Int. Cl.
*H04B 10/114* (2013.01)
*H04B 13/00* (2006.01)

(52) U.S. Cl.
CPC ......... *H04B 10/114* (2013.01); *H04B 13/005* (2013.01)

(58) Field of Classification Search
None
See application file for complete search history.

(56) References Cited

U.S. PATENT DOCUMENTS 4,677,982 A * 7/1987 Llinas ................. A61B 5/0017
                                                       398/107
5,320,098 A    6/1994 Davidson
(Continued)

FOREIGN PATENT DOCUMENTS

CN       101910911 A      12/2010
CN       106255527 A      12/2016
(Continued)

OTHER PUBLICATIONS

Sackinger, Eduard, Broadband Circuits for Optical Fiber Communication, 2002 (Year: 2002).*
(Continued)

*Primary Examiner* — Jai M Lee
(74) *Attorney, Agent, or Firm* — Hamilton, Brook, Smith & Reynolds, P.C.

(57) ABSTRACT

In an example embodiment, an optical communication system includes an implantable optical transmitter and an external optical receiver. The transmitter includes a housing having one or more drivers, plural light emitting sources, and an optical element arranged therein. Each driver converts a digital data signal into modulation signals to drive the sources. Each source generates a light beam in response to a corresponding modulation signal, each light beam contributing to form a single optical signal. The optical element directs the light beams to exit the housing such that a peak position of light intensity of each light beam is separated from a corresponding peak position of light intensity of an adjacent light beam by at least a first distance and less than a second distance. The optical receiver includes at least one photodiode that detects light generated by the sources and generates a reconstructed data signal.

33 Claims, 8 Drawing Sheets

Related U.S. Application Data

(60) Provisional application No. 62/915,967, filed on Oct. 16, 2019.

(56) References Cited

U.S. PATENT DOCUMENTS

| | | | |
|---|---|---|---|
| 5,387,259 A | 2/1995 | Davidson | |
| 5,526,160 A | 6/1996 | Watanabe et al. | |
| 5,726,786 A * | 3/1998 | Heflinger | H04B 10/1149 398/127 |
| 6,049,727 A * | 4/2000 | Crothall | A61B 5/6876 600/316 |
| 6,243,608 B1 * | 6/2001 | Pauly | A61N 1/37217 128/903 |
| 6,349,234 B2 | 2/2002 | Pauly et al. | |
| 6,671,528 B2 * | 12/2003 | Steuer | A61B 5/6838 600/335 |
| 6,898,464 B2 * | 5/2005 | Edell | A61B 5/0017 128/903 |
| 7,280,870 B2 | 10/2007 | Nurmikko et al. | |
| 7,647,097 B2 | 1/2010 | Flaherty et al. | |
| 8,036,736 B2 | 10/2011 | Snyder et al. | |
| 9,061,134 B2 | 6/2015 | Askin et al. | |
| 9,350,448 B2 * | 5/2016 | Byers | H04B 10/1149 |
| 9,509,400 B2 * | 11/2016 | Jain | H04J 14/02 |
| 9,907,496 B1 * | 3/2018 | Okandan | A61B 5/1459 |
| 9,936,876 B2 * | 4/2018 | Jain | A61B 5/1459 |
| 10,433,754 B2 | 10/2019 | Nurmikko et al. | |
| 10,820,845 B2 * | 11/2020 | Papadimitrakopoulos | A61B 5/15003 |
| 11,234,078 B1 * | 1/2022 | Silfvast | H04S 1/007 |
| 11,575,434 B2 * | 2/2023 | Burdin | A61B 5/0017 |
| 11,589,748 B2 * | 2/2023 | Maharbiz | A61B 5/076 |
| 2005/0279739 A1 | 12/2005 | Bruland et al. | |
| 2007/0100398 A1 | 5/2007 | Sloan | |
| 2009/0163968 A1 | 6/2009 | Donofrio | |
| 2009/0248106 A1 * | 10/2009 | Black | H04B 10/807 607/46 |
| 2010/0272299 A1 | 10/2010 | Van Schuylenbergh et al. | |
| 2011/0062125 A1 | 3/2011 | Park et al. | |
| 2011/0092842 A1 | 4/2011 | Decaria et al. | |
| 2012/0029414 A1 * | 2/2012 | Wolf, II | A61M 27/006 604/9 |
| 2012/0116155 A1 * | 5/2012 | Trusty | H04B 10/1143 600/109 |
| 2013/0177316 A1 | 7/2013 | Cardakli | |
| 2014/0072308 A1 | 3/2014 | Jain et al. | |
| 2014/0094674 A1 * | 4/2014 | Nurmikko | A61N 1/3787 607/45 |
| 2015/0265182 A1 * | 9/2015 | Jain | A61B 5/14539 606/129 |
| 2015/0304027 A1 | 10/2015 | Nciri | |
| 2017/0202466 A1 | 7/2017 | Paulussen et al. | |
| 2017/0319096 A1 | 11/2017 | Kaiser et al. | |
| 2017/0340243 A1 * | 11/2017 | Jain | A61B 5/0084 |
| 2018/0153474 A1 | 6/2018 | Aeschlimann et al. | |
| 2021/0007602 A1 | 1/2021 | Seo et al. | |
| 2021/0177311 A1 * | 6/2021 | Schaefer | A61B 5/1455 |
| 2022/0368418 A1 | 11/2022 | Burdin et al. | |

FOREIGN PATENT DOCUMENTS

| | | |
|---|---|---|
| CN | 205829628 U | 12/2016 |
| CN | 107193123 A | 9/2017 |
| CN | 108476067 A | 8/2018 |
| CN | 110177503 A | 8/2019 |
| EP | 0261834 A2 | 3/1988 |
| EP | 3609397 A1 | 2/2020 |
| JP | 2013-242405 A | 12/2013 |
| WO | 2012/126003 A1 | 9/2012 |
| WO | 2015038352 A1 | 3/2015 |
| WO | 2018032060 A1 | 7/2019 |
| WO | 2019200918 A1 | 10/2019 |
| WO | 2019211314 A1 | 11/2019 |
| WO | 2020086473 A1 | 4/2020 |
| WO | 2021/074866 A1 | 4/2021 |

OTHER PUBLICATIONS

Xiao Pingping, "Wireless optical communication practice Development of testing system", Journal of Jiangxi Normal University (Natural Science Edition), vol. 31(6), Nov. 15, 2007.

Ackermann, et al., "Designing the Optical Interface of a Transcutaneous Optical Telemetry Link", IEEE Transactions on Biomedical Engineering, IEEE Service Center, Piscataway, NJ, USA, vol. 55, No. 4, Apr. 1, 2008 (Apr. 1, 2008). pp. 1365-1373.

PCT International Search Report and Written Opinion for International Application No. PCT/IB2020/059735, entitled "Optical Transmission For An Implantable System," dated Jan. 13, 2021.

Guillory, et al., "Hybrid RF/IR Transcutaneous Telemetry for Power and High-Bandwith Data," Proceedings of the 26th Annual International Conference of the IEEE EMBS, San Francisco, CA, Sep. 1-5, 2004, pp. 4338-4340.

Liu, et al., "In Vivo Verification of a 100 Mbps Transcutaneous Optical Telemetric Link," 2014 IEEE Biomedical Circuits and Systems Conference (BioCAS) Proceedings, Oct. 22-24, 2014, 978-1-4799-2346-5.

Parmentier, et al., "Laser Diode Used in 16 Mb/s, 10 mW Optical Transcutaneous Telemetry System," 2008 IEEE Biomedical Circuits and Systems Conference, Nov. 20-22, 2008, 2163-4025.

* cited by examiner (SECTION A-A)

OPTICAL TRANSMISSION FOR AN IMPLANTABLE SYSTEM

RELATED APPLICATION

This application is a continuation of U.S. application Ser. No. 17/765,312, filed Mar. 30, 2022, which is a continuation of U.S. National Stage of International Application No. PCT/IB2020/059735, filed Oct. 15, 2020, which designates the U.S., published in English, and claims the benefit of U.S. Provisional Application No. 62/915,967, filed on Oct. 16, 2019. The entire teachings of the above applications are incorporated herein by reference.

BACKGROUND

Monitoring devices designed for implant in the human body require a way to transmit the data that they collect to an external device so that the collected data can be processed. Typically, such implantable devices employ optical or radio frequency transmission.

SUMMARY

Embodiments of the present disclosure are directed to allowing a safe and robust optical transfer of data through biological tissues with a high throughput and high penetration depth, while being highly tolerant to misalignment and minimizing optical power density and tissue temperature increase.

An example embodiment includes multiple light sources separated by a certain distance within an implanted hermetic housing, with multiple robust low-profile optical windows that allow light to exit the hermetic housing and to be safely injected into the biological tissue. The optical window geometry and/or surface properties may be adjusted to positively influence light propagation through the tissue. One or more photodiodes receive the optical signal on the other side of the tissue and convert the received optical signal into an electric signal. The electrical signal is amplified by one or more amplifiers that feed a clock and data recovery stage.

According to an example embodiment, a transcutaneous optical communication system includes an implantable optical transmitter device and an external optical receiver device.

The implantable optical transmitter device may include a hermetic housing having a cavity, a distal end, and a proximal end, the cavity including one or more drivers, plural light emitting sources, and an optical element arranged therein. Each of the one or more drivers is configured to convert a digital data signal into one or more modulation signals to drive one or more of the light emitting sources. Each light emitting source is configured to generate a light beam in response to a corresponding one of the one or more modulation signals, each light beam contributing to form a single optical signal. The optical element is configured to direct the light beams to exit the proximal end of the hermetic housing distributed in a pattern in which a peak position of light intensity of each light beam is separated from a corresponding peak position of light intensity of an adjacent light beam by at least a first distance and less than a second distance.

The external optical receiver device may include at least one photodiode configured to detect light generated by the plural light emitting sources and to responsively generate an external detection signal, amplifier circuitry configured to amplify the external detection signal, and clock and data recovery circuitry coupled to receive the amplified detection signal and configured to generate a reconstructed data signal.

According to an example embodiment, a method for transcutaneous optical communication includes, at an implantable optical transmitter device, converting a digital data signal into one or more modulation signals, generating a light beam in response to a corresponding one of the one or more modulation signals, each light beam contributing to form a single optical signal, and directing the light beams to exit the implantable optical transmitter device distributed in a pattern in which a peak position of light intensity of each light beam is separated from a corresponding peak position of light intensity of an adjacent light beam by at least a first distance and less than a second distance.

The method may further include, at an external optical receiver device positioned to detect one or more of the light beams, detecting light generated by the plural light emitting sources and responsively generating an external detection signal, amplifying the external detection signal, and receiving the amplified detection signal and generating a reconstructed data signal.

According to an example embodiment, an implantable device comprises a hermetic housing having a cavity, a distal end, and a proximal end, the cavity including one or more drivers, plural light emitting sources, and an optical element arranged therein. Each of the one or more drivers is configured to convert a digital data signal (representing a physiological signal) into one or more modulation signals to drive one or more of the light emitting sources. Each light emitting source is configured to generate a light beam in response to a corresponding one of the one or more modulation signals, each light beam contributing to form a single optical signal. The optical element is configured to direct the light beams to exit the proximal end of the hermetic housing distributed in a pattern in which a peak position of light intensity of each light beam is separated from a corresponding peak position of light intensity of an adjacent light beam by at least a first distance and less than a second distance.

The implantable device may be configured to be embedded within biological tissue and the first distance and the second distance are based on characteristics of the biological tissue.

In an example embodiment, the first distance may be greater than 0.5 millimeters and the second distance less than 50 millimeters.

In an example embodiment, the optical element comprises plural optical windows. Each optical window of the plural optical windows may comprise a lens, an anti-reflective coating, a diffusing layer, a micro-structured surface, or any combination thereof.

The implantable device may further include a ferrule positioned at the proximal end of the housing and configured to contain the plural optical windows, the ferrule having plural openings aligned with the plural optical windows, the plural optical windows recessed from a top surface of the ferrule.

The plural light emitting sources may comprise N light emitting sources, and the plural optical windows may comprise M optical windows, with N greater than or equal to M.

In an example embodiment, the optical element comprises a single optical window. The single optical window may comprise a lens, an anti-reflective coating, a diffusing layer, a micro-structured surface, or any combination thereof.

The implantable device may further include a ferrule having plural openings, the ferrule positioned at the proximal end of the housing and the single optical window recessed from the proximal end of the housing by at least a thickness of the ferrule.

The plural light emitting sources may comprise N light emitting sources, and the plural openings may comprise M openings, with N greater than or equal to M.

The one or more drivers may be configured to operate based on on-off keying modulation and/or multiple amplitude shift keying modulation.

The implantable device may further include analog front-end circuitry configured to convert a physiological signal to the digital data signal.

According to an example embodiment, a transcutaneous optical communication system includes an external optical transmitter device and an implantable optical receiver device.

The external optical transmitter device may include a housing having one or more drivers, plural light emitting sources, and an optical element arranged therein. Each of the one or more drivers is configured to convert a digital data signal into one or more modulation signals to drive one or more of the light emitting sources. Each light emitting source is configured to generate a light beam in response to a corresponding one of the one or more modulation signals, each light beam contributing to form a single optical signal. The optical element is configured to direct the light beams to exit the housing distributed in a pattern in which a peak position of light intensity of each light beam is separated from a corresponding peak position of light intensity of an adjacent light beam by at least a first distance and less than a second distance.

The implantable optical receiver device may include at least one photodiode configured to detect light generated by the plural light emitting sources and to responsively generate an external detection signal, amplifier circuitry configured to amplify the external detection signal, a receiver coupled to receive the amplified detection signal and configured to generate a reconstructed data signal, a controller configured to convert the reconstructed data signal to a controller signal, and a stimulation generator configured to generate a stimulation signal based on the controller signal.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
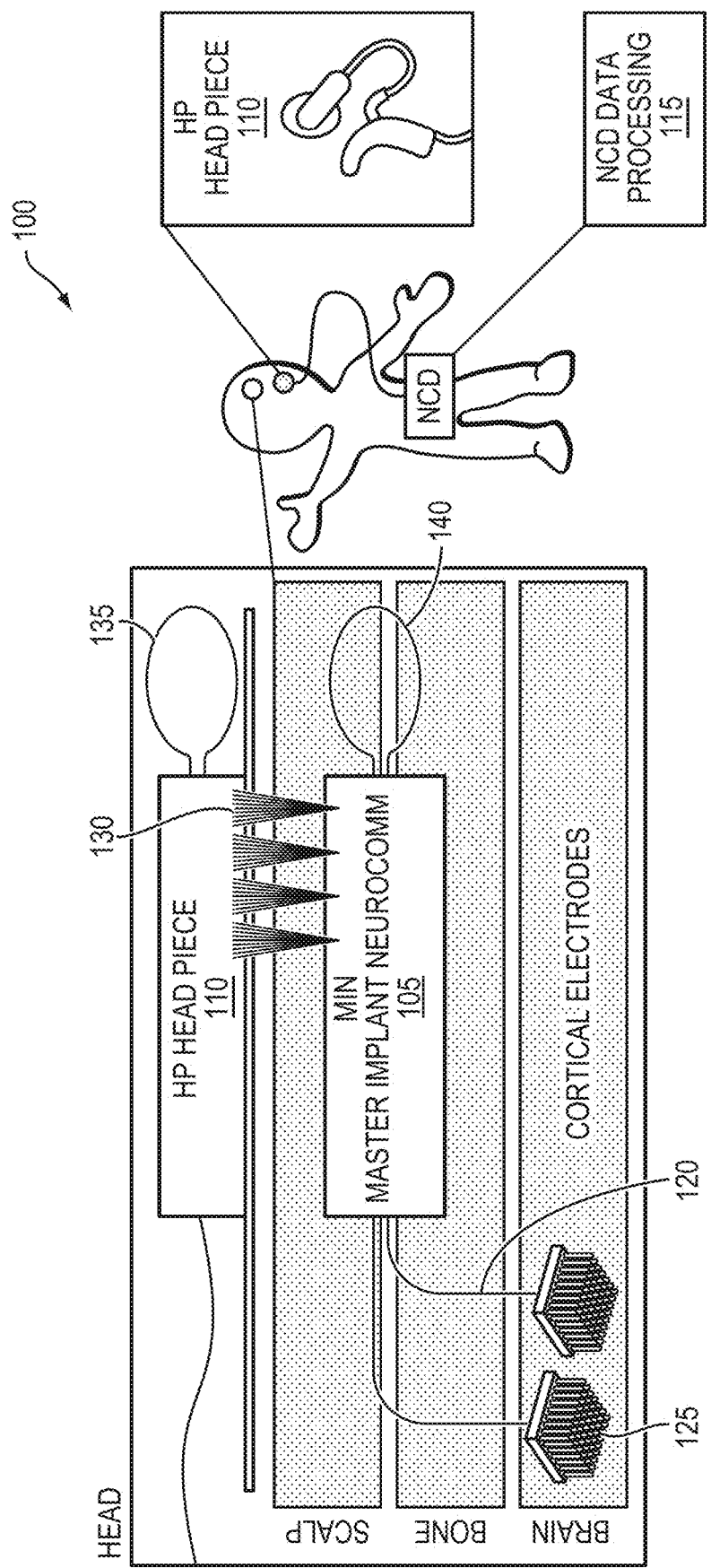
FIG. 1 shows a conceptual view of a transcutaneous optical communication system.

FIG. 1 illustrates a conceptual view of a transcutaneous communication system 100. The system 100 includes a master implant neuro-communicator (MIN) 105, an external head piece (HP) or wearable device 110, and a data processing device (NCD) 115. As shown conceptually, the MIN 105 is implanted under a patient's scalp and has signal wires 120 coupled to cortical electrodes 125 in contact with a portion of the patient's brain cortex. The MIN 105 converts physiological signals received on the signal wires 120 to an optical signal 130 that is transmitted to the HP 110 through the scalp. The HP 110 receives the optical signal on the other side of the scalp and converts the received optical signal into an electric signal. The electrical signal is amplified by one or more amplifiers, which feed a clock and data recovery stage to produce a reconstructed data signal. The NCD 115 is configured for data processing functions on the reconstructed data signal. The HP 110 is configured to power and control the MIN 105 via coils 135, 140.

Figure 2:
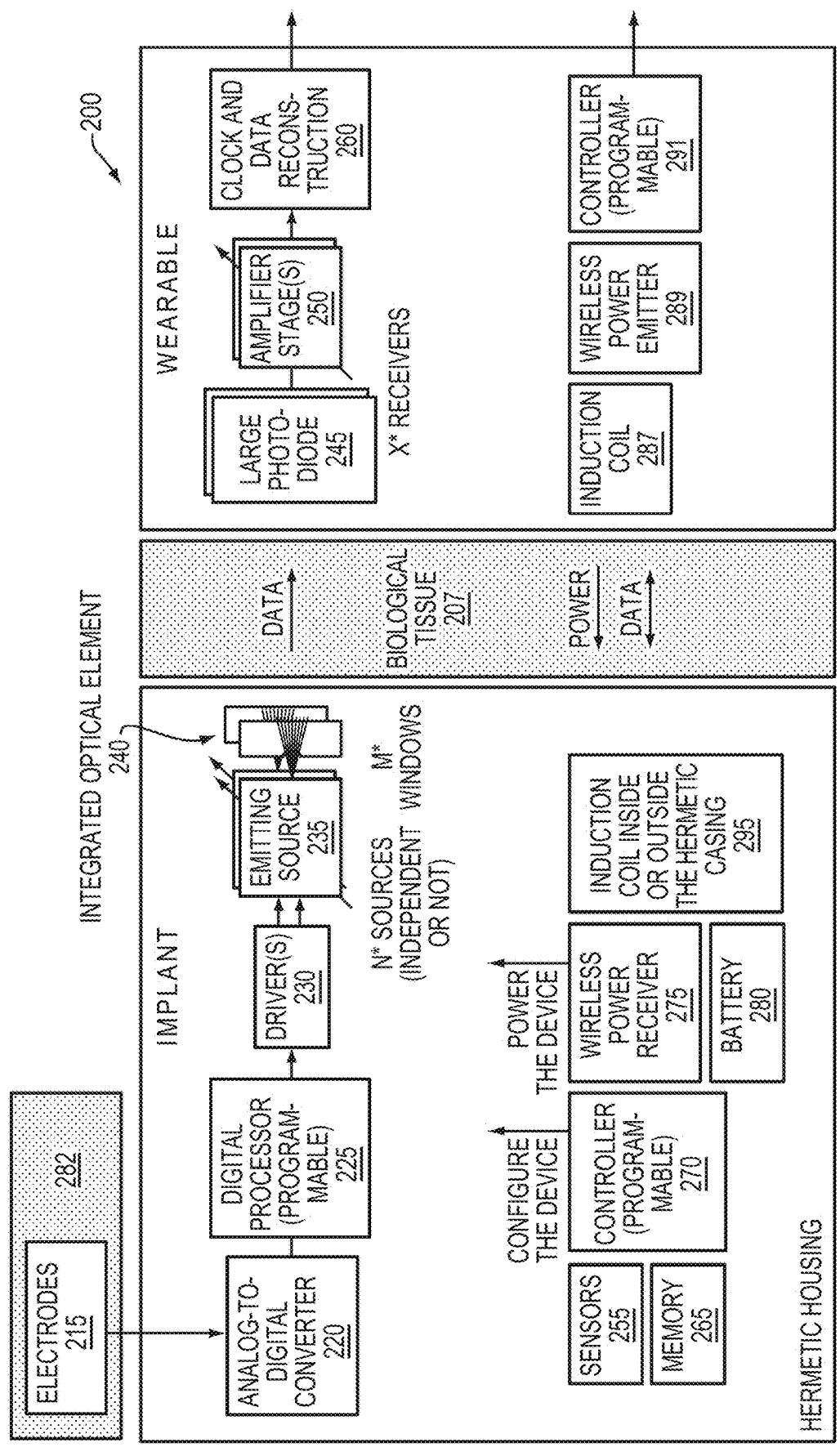
FIG. 2 illustrates a block diagram of a first embodiment of a transcutaneous optical communication system.

FIG. 2 illustrates a block diagram of a first example embodiment of a transcutaneous communication system 200. The system 200 includes an implantable device or a master implant neuro-communicator (MIN) 205 and an external wearable device 210. The MIN 205 has a hermetic housing (not shown) that includes an analog-to-digital converter (ADC) 220, a programmable digital signal processor (DSP) 225, one or more drivers 230, plural light emitting sources 235, and an integrated optical element 240 that includes plural windows. Electrodes 215 provide analog physiological signals to the ADC 220 when attached to a patient's cortical region 282. It should be understood that other regions of the body can also be contemplated for use with embodiments configured based on functions and elements of the MIN 205.

The MIN 205 may further include sensors 255, memory 265, a controller 270 for configuring the MIN 205, a wireless power receiver 275 for powering the MIN 205, battery 280, and an induction coil 295.

The sensors 255 may include temperature sensors, humidity sensors, voltage and current sensors, accelerometers, etc. The sensors 255 are useful for monitoring the MIN 205 and to ensure safety.

The memory 265 may be arranged to store the implant's configurations, firmware, implant and/or patient information (e.g., name, serial number) and/or to log data (e.g., battery voltage, temperature, humidity, time, events).

The controller 270 may be a programmable microcontroller arranged to configure acquisition, the DSP 225, and the drivers. In addition, the controller 270 may be configured to read the sensors 255, to write/read the memory 265, to manage the communication with the wearable 210, and to upgrade the implant's firmware.

The wireless power receiver 275 is configured to convert AC voltage from induction coil 295 into rectified and regulated clean voltages (DC) to power the implant's electronics.

The battery 280 in some embodiments can store energy to be used during power interruption, or to power the MIN 205 when the wearable 210 is absent to keep some functions running.

The induction coil 295 is configured to convert an alternating magnetic field into an alternating electrical signal.

The wearable device 210 includes one or more photodiodes 245, one or more amplifier stages 250, and clock and data recovery circuitry 260.

The wearable device 210 further includes an induction coil 287, a wireless power emitter 289, and a controller 291.

In operation, the ADC 220 converts the analog physiological signal received from electrodes 215 to a digital signal. The ADC function may be provided by, for example, an analog front end (AFE) chip. The DSP 225 processes the digital signal. The DSP 225 controls the ADC 220, reads the result of the analog-to-digital conversions, encapsulates the data with a header and a checksum to ensure data integrity and sends the data to one or more drivers 230. The output of the DSP 225 is coupled to the one or more drivers 230 which convert the digital signal to one more modulation signals to drive the plural light emitting sources 235. The light beams emitted from the emitting sources 235 contribute to form a single optical signal. The integrated optical element 240 has multiple robust low profile optical windows that allow the optical signal to exit the hermetic housing and to be safely injected into the biological tissue 207. At the wearable device 210, one or more photodiodes 245 receive the optical signal on the other side of the tissue and convert the received optical signal into an electric signal. In alternative embodiments, other types of optical receivers are used in place of the photodiodes 245. The electrical signal is amplified by one or more amplifiers 250, which feed a clock and data recovery or reconstruction stage 260. The reconstructed data signal exits 262 the wearable device 210 for further processing.

The wearable device 210 may be configured to transfer power from wireless power emitter 289 to the wireless power receiver 275 at MIN 205 via the induction coils 287, 295. In addition, the wearable device 210 may be configured to program and communicate with the controller 270 at MIN 205 from controller 291 via the induction coils 287, 295.

Target Data Rate

New applications of implantable devices require large amounts of information to transit across the patient's tissue, which can typically occur at a date transfer rate of more than 25 Mbps, given the number of channels, sampling rate, and resolution required.

Skin Thickness

The optical power that needs to be transmitted through tissue is affected by tissue thickness and type. In an example of potential application of device implanted in a patient's head, the tissue thickness can be typically 7 to 8 mm in average, reaching up to 12 mm, or even more.

Wavelengths

The skin absorption and scattering coefficients are not constant and vary with the wavelength. The ability of light to penetrate biological tissues depends also on tissue components such as pigments, melanin, fat, water, and oxy/deoxy blood. Therefore, the wavelength is chosen to be able to maximize the transmitted energy, but the link is also configured to be flexible and tolerant enough to accommodate all skin variations.

Many publications identified a "near-infrared window" in biological tissues, between 600 nm and 1300 nm. At these wavelengths, the combination of the melanin, the water, and the blood absorbs less light than at shorter or longer wavelengths. Plus, the scattering coefficient of biological tissues decreases when the wavelength increases. In some embodiments, the wavelength may be in the range between 400 nm and 1400 nm.

Emitting Source

The optical communication link, unidirectional, is based on multiple fast emitting infrared sources, for power adjustment and redundancy (and to decrease the power density by spreading the power over the multiple sources), modulated by the digital data with the operation of a driver. The scalp thickness, absorption, and scattering properties can be compensated by an adjustable emitting source and an adjustable receiver sensitivity. Therefore, it is possible to optimize the bit error rate while keeping the power consumption as low as possible.

The emitting sources 235 can be light emitting diodes (LEDs) or vertical-cavity surface-emitting lasers (VCSELs). Both are types of emitting sources that can emit infrared radiations in a small form factor. While LEDs are typically limited to 20 Mbps, VCSELs can achieve a data rate up to several Gbps.

Driver

In an embodiment, the driver(s) 230 may be a very simple and high-speed transistor used to modulate the VCSEL current with a power efficient and simple On Off Keying (OOK) modulation. The multiple emitting sources can also be operated using multiple amplitude shift keying (M-ASK).

Wearable Photodiode

The photodiode 245 may be, for example, a Hamamatsu S6967 photodiode, which has a 50 MHz bandwidth, a sensitivity of about 0.62 W/A at 850 nm, a photosensitive area of 26.4 $mm^2$, and a large viewing angle of more than 120°. Placing the photodiode 245 as close as possible to the skin has the advantage of providing a large viewing angle, which also aids with alignment to the emitting sources. The goal is to be able to capture all the diffused light reaching the surface of the skin, even if the photons arrive with a significant incident angle. An optical system (e.g., Fresnel lens, lens, filter) (not shown) may be added to the photodiode to capture more photons or to select only the wavelength of interest.

Amplifier Stages

The photodiode 245 delivers a current proportional to the optical power received. The amplifier stage(s) 250 transform this current into a voltage.

In an experimental configuration to demonstrate the concepts of the implantable devices described herein, solid optical phantoms have been used to mimic the optical properties of the tissue. Nominal and extreme cases for optical properties and tissue thickness (2 mm and 15 mm representing the extremes for skin thickness) have been used.

Figure 3B:
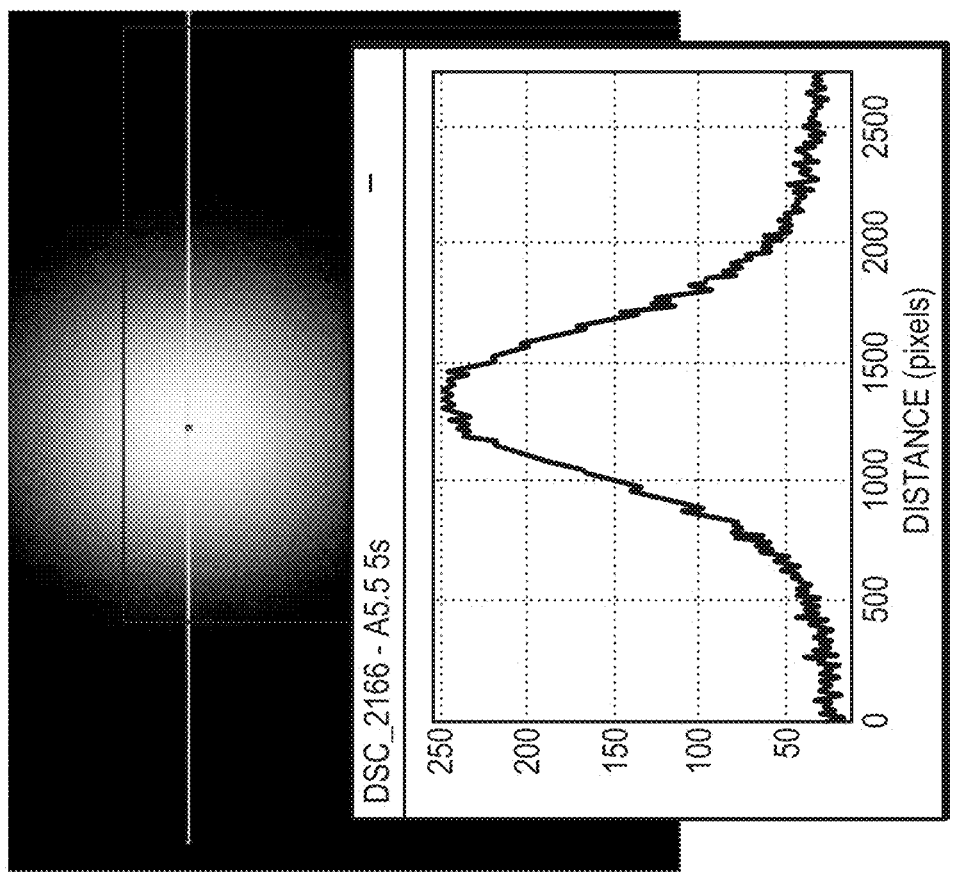
FIGS. 3A-3B illustrate an optical beam shape after going through optical phantoms in an experimental configuration.
Figure 3A:
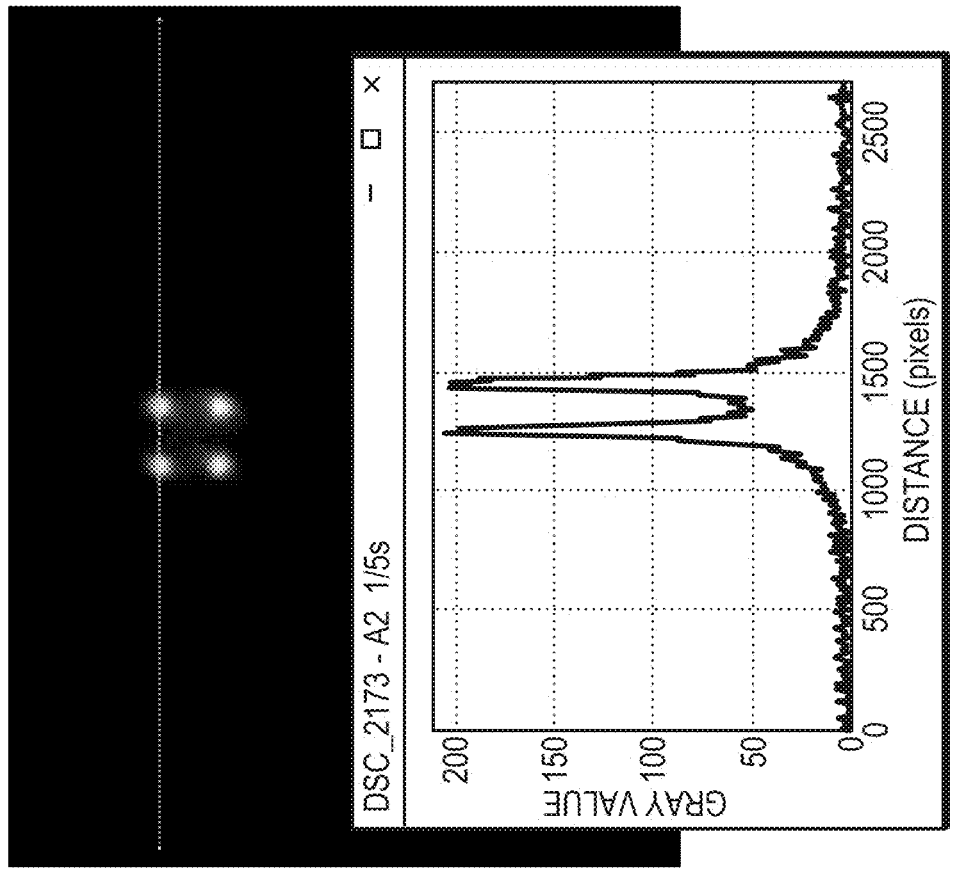

FIGS. 3A-3B illustrate the shape of the beam after going through optical phantoms in the experimental configuration. FIG. 3A shows results for an optical phantom A2, which is 2 mm thick, and FIG. 3B shows results for an optical phantom A5.5, which is 5.5 mm thick. For the A2 phantom, distinct optical beams from four emitter sources can be seen separated. For phantoms thicker than 2 mm, such as the A5.5 phantom, the beams are intersecting and summed to form a single peak, as shown by FIG. 3B, thanks to the scattering effect. Therefore, for thin skin the multiple sources concept increases the alignment tolerance, and for thick skins the total beam formed is a combination of the four beams, and the alignment tolerance is probably larger due to the scattering coefficient.

It has been found that, in order to accommodate ranges of thickness of the biological tissue 207 (FIG. 2), the emitting sources are separated such that the light beams that exit the hermetic housing are distributed in a pattern in which a peak position of light intensity of each light beam is separated from a corresponding peak position of light intensity of an adjacent light beam by at least a first distance and less than a second distance. For example, the first distance may be greater than 0.5 mm, and the second distance may be less than 50 mm.

Figure 4C:
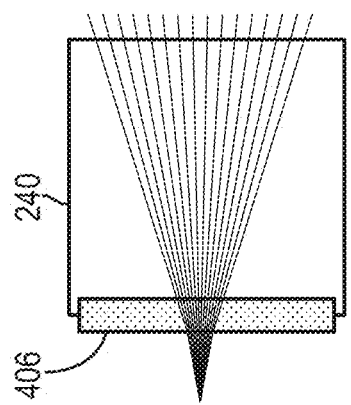
FIGS. 4A-4D show several example arrangements for an optical element.
Figure 4D:
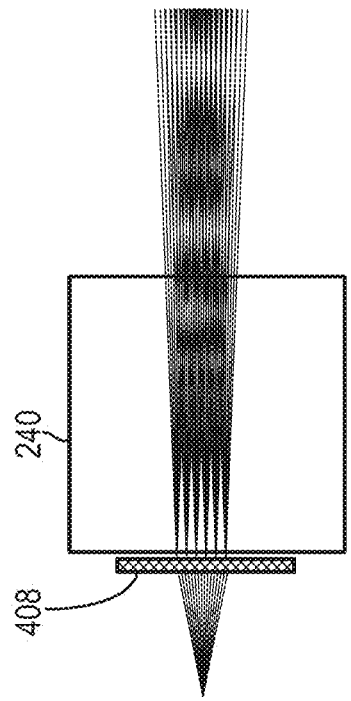
Figure 4A:
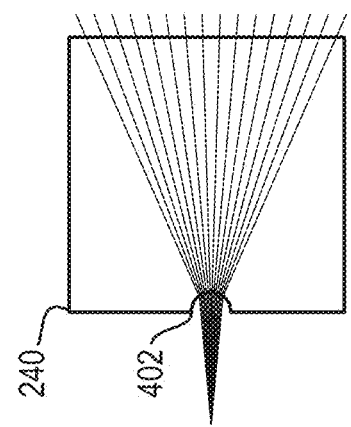
Figure 4B:
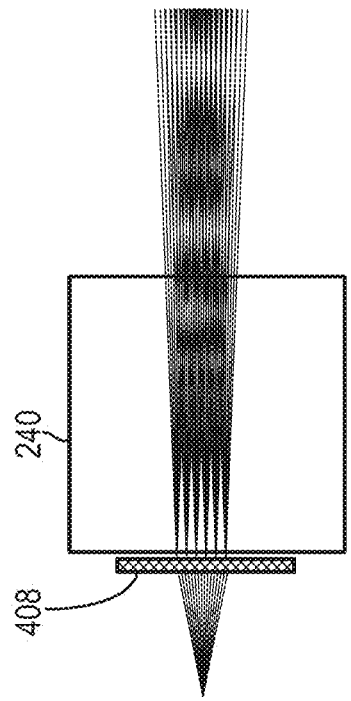

The integrated optical element 240 can be, for example, constructed from sapphire or other suitable material. FIGS. 4A-4D show several example arrangements for the optical element 240. In FIG. 4A the optical element includes a lens 402 such as a plano-concave lens. In FIG. 4B an anti-reflective coating 404 (e.g., thin film or thick film) is applied to a surface of the optical element 240 to reduce reflection and therefore increase the transmitted energy. In FIG. 4C a diffusing layer 406, such as a frosted surface, is applied to a surface of the optical element 240. In FIG. 4D the optical element 240 includes a micro-structured or micro-patterned surface 408.

Figure 5B:
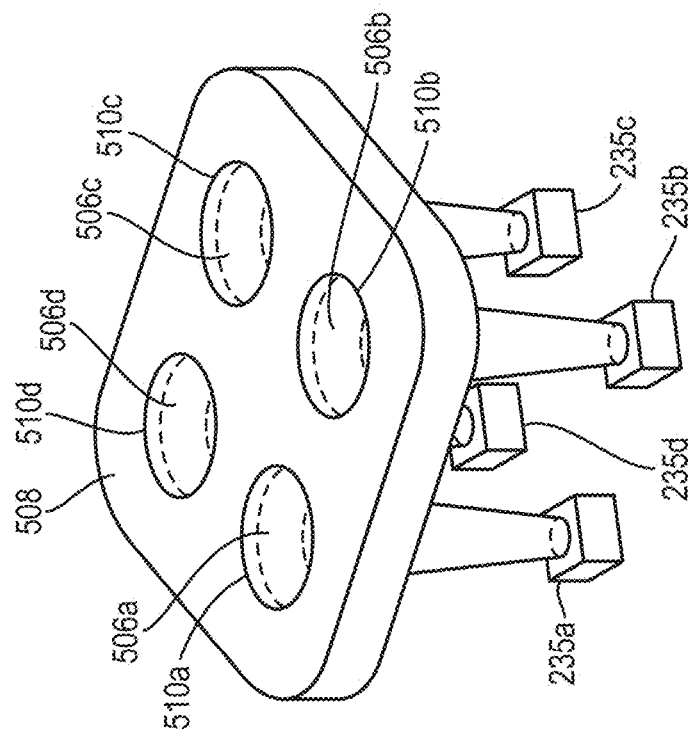
FIGS. 5A-5B show example arrangements of an optical element in which four emitting sources are employed.
Figure 5A:
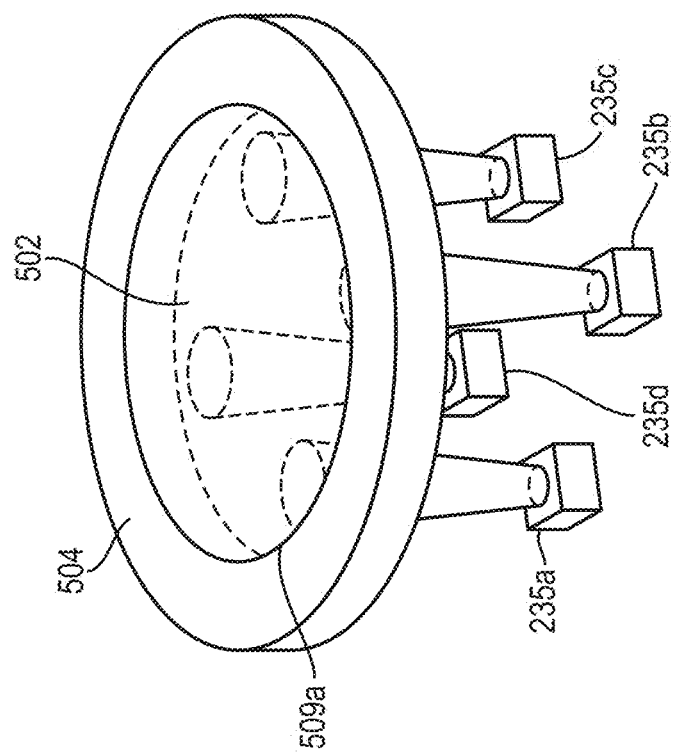
Figure 6:
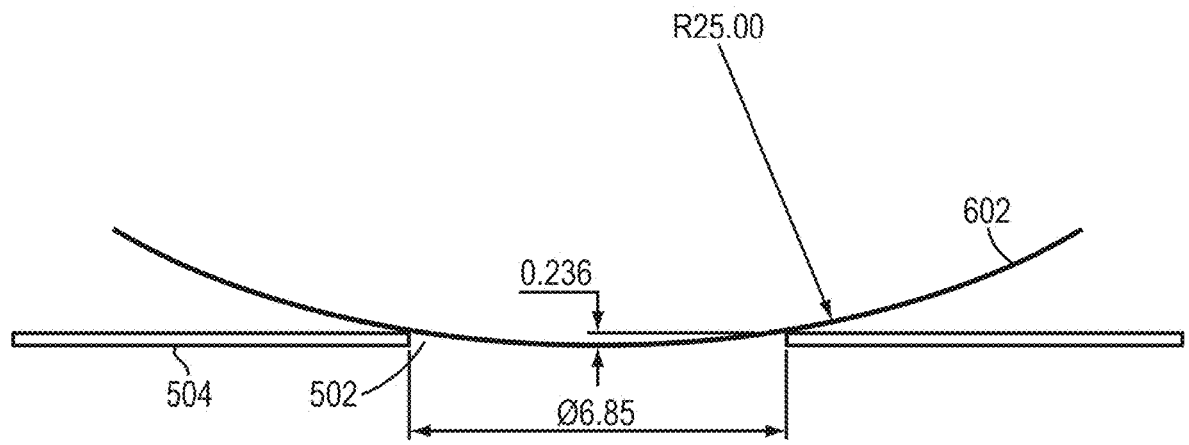
FIGS. 6 and 7 show example arrangements of an impactor in relation to example optical windows.
Figure 7:
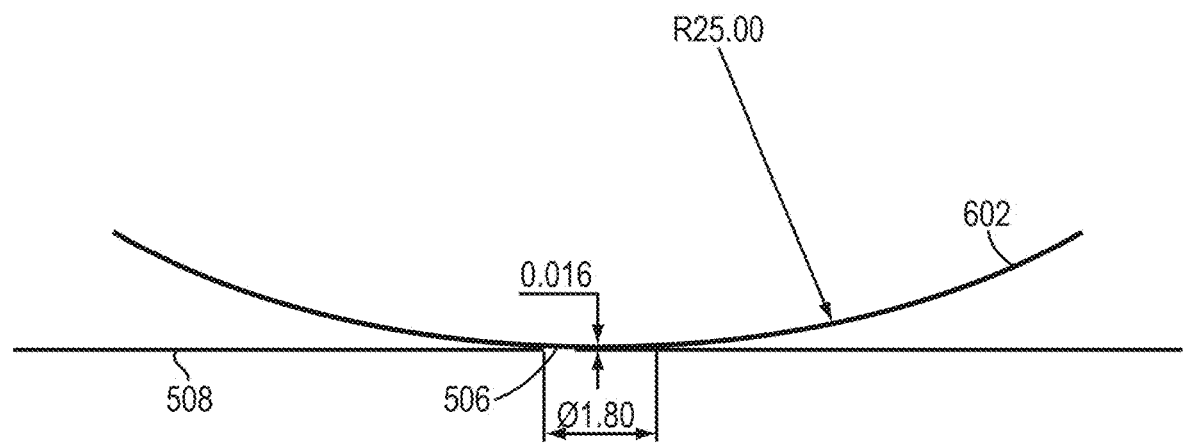

FIGS. 5A-5B show two example arrangements of the optical element 240 in which four emitting sources 235a-235d are employed. In FIG. 5A the optical element comprises a single window 502 held in place by a ferrule 504 having a single opening 509a. In FIG. 5B the optical element comprises four windows 506a-506d held in place by a ferrule 508 having four corresponding openings 510a-510d. Each one of the multiple optical windows 506a-506d, covering a subset of infrared emitting sources 235a-235d, can have a smaller diameter than a single window covering all sources. For a given thickness, multiple windows have a lower diameter-to-thickness ratio than a single larger window, therefore being more mechanically robust. Similarly, with a given recess distance from the surface of the windows to the surface of their supporting ferrule, an impactor having a given concave surface can directly hit the surface of the larger single window, while avoiding the surface of the smaller ones. Put another way, for a given impactor with a given concave surface, the surface of the larger single window needs to be recessed further than the surface of the smaller windows to avoid an impact. This concept is shown in FIGS. 6 and 7, which show an impactor 602 having radius 25 mm. In FIG. 6, the large window 502 having a 6.85 mm diameter is recessed by 0.236 mm. By contrast, in FIG. 7 the small window 506 having a 1.80 mm diameter only needs to be recessed by 0.016 mm to avoid the impactor 602. An advantage of the smaller window 506 is that the packaging of the implantable device can be made smaller since the recess is smaller.

The combination of a direct impact and a high diameter-to-thickness ratio generates an increased probability of damage to the window, possibly resulting in a loss of hermeticity: recess distance and/or window thickness would need to be increased to avoid that, and both these options would hinder the "low profile" aspect.

Figure 8B:
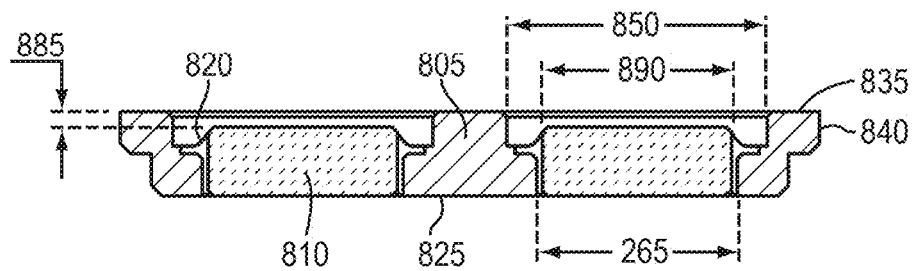
FIGS. 8A-8B illustrate in more detail an example multiple window and ferrule arrangement.
Figure 8A:
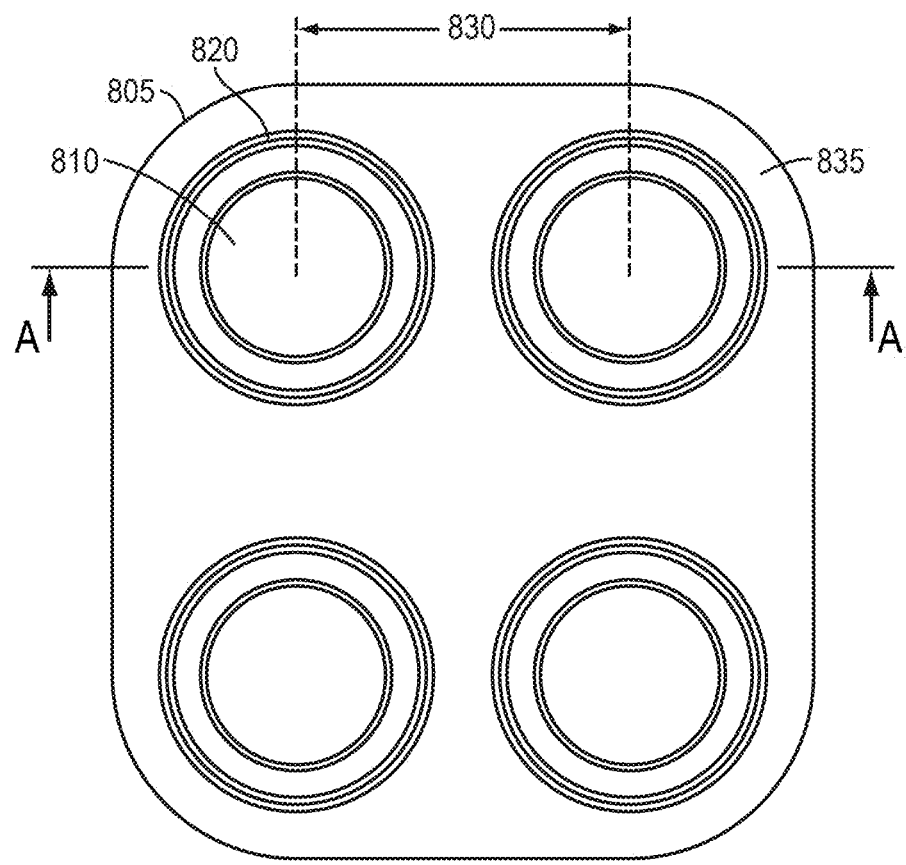

FIGS. 8A-8B illustrate in more detail an example multiple window and ferrule arrangement. FIG. 8A is a plan view that shows ferrule 805 holding four sapphire windows 810. The ferrule 805 may be made from titanium or other suitable material. The centers of the windows 810 are separated by a distance 830. As shown in the cross-sectional view (FIG. 8B) through a cutting plane A-A illustrated by lines A-A, the windows 810 are recessed from the top 835 of the ferrule by a distance 885. In this embodiment, the windows 810 are not recessed from the bottom 825 of the ferrule, but in other embodiments, the windows may be recessed from bottom also. The ferrule is bonded to each window 810 by a hermetic seal 820, by means of a pure gold brazing for example, and includes a flange 840 for seating the ferrule in the housing. The distance 830 between centers of windows 810 is selected to correspond with placement of the one or more emitting sources 235 (FIG. 2) for alignment with the windows 810.

Figure 9:
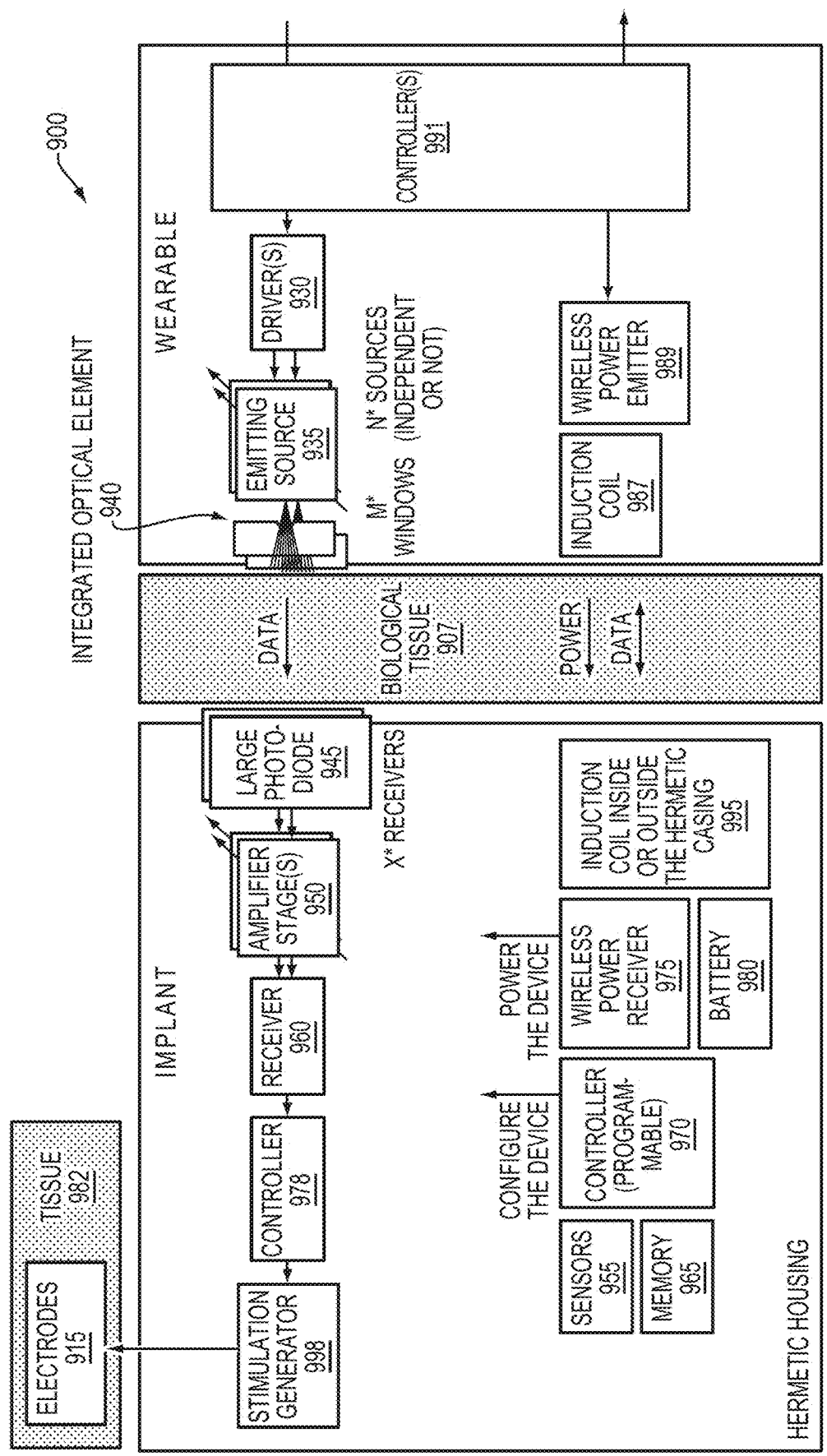
FIG. 9 illustrates a block diagram of a second embodiment of a transcutaneous optical communication system.

FIG. 9 illustrates a block diagram of a second example embodiment of a transcutaneous optical communication system. In this system 900, optical communication is directed from a wearable device 910 to an implant device 905. Such a system 900 may be configured to deliver stimulation signals internally to an area of tissue. In addition, the system 900 may be configured to provide service signals for programming, upgrading and/or changing parameters of the implant device 905.

The implant device 905 has a hermetic housing (not shown) that includes one or more photodiodes 945, one or more amplifier stages 950, receiver 960, controller 978, and stimulation generator 998. Electrodes 915 provide analog physiological signals from stimulation generator 998 when attached to a tissue region of a patient.

The implant device 905 may further include sensors 955, memory 965, a controller 970 for configuring the implant device 905, a wireless power receiver 975 for powering the implant device 905, battery 980, and an induction coil 995.

The sensors 955 may include temperature sensors, humidity sensors, voltage and current sensors, accelerometers, etc. The sensors 955 are useful for monitoring the implant device 905 and to ensure safety.

The memory 965 may be arranged to store the implant's configurations, firmware, implant and/or patient information (e.g., name, serial number) and/or to log data (e.g., battery voltage, temperature, humidity, time, events).

The controller 970 may be a microcontroller arranged to configure controller 978. In addition, the controller 970 may be configured to read the sensors 955, to write/read the memory 965, to manage the communication with the wearable 910 and to upgrade the implant's firmware.

The wireless power receiver 975 is configured to convert AC voltage from induction coil 995 into rectified and regulated clean voltages (DC) to power the implant's electronics.

The battery 980 in some embodiments can store energy to be used during power interruption, or to power the implant device 905 when the wearable 910 is absent to keep some functions running.

The induction coil 995 is configured to convert an alternating magnetic field into an alternating electrical signal.

The wearable device 910 includes one or more drivers 930, plural light emitting sources 935, and an integrated optical element 940 that includes plural windows.

The wearable device 910 further includes an induction coil 987, a wireless power emitter 989, and a controller 991.

In operation, the controller 991 provides a digital signal to the one or more drivers 930 which convert the digital signal to one more modulation signals to drive the plural light emitting sources 935. The light beams emitted from the emitting sources 935 contribute to form a single optical signal. The integrated optical element 940 has multiple robust low profile optical windows that allow the optical signal to exit the wearable device 910 and to be safely injected into the biological tissue 907. At the implant device 905, one or more photodiodes 945 receive the optical signal on the other side of the tissue and convert the received optical signal into an electric signal. The electrical signal is amplified by one or more amplifiers 950 that feed a receiver 960. The reconstructed data signal is coupled to controller 978, which is programmed to control the stimulation generator 998 to provide stimulation signals to tissue 982.

The wearable device 910 may be configured to transfer power from wireless power emitter 989 to the wireless power receiver 975 at implant device 905 via the induction coils 987, 995. In addition, the wearable device 910 may be configured to program the controller 970 from controller 991 via the induction coils 987, 995.

While example embodiments have been particularly shown and described, it will be understood by those skilled in the art that various changes in form and details may be made therein without departing from the scope of the embodiments encompassed by the appended claims.

What is claimed is:

1. A transcutaneous optical communication system comprising:
    an implantable optical transmitter device including:
        one or more drivers, plural light emitting sources, and an optical element;
        each of the one or more drivers configured to convert a digital data signal into one or more modulation signals to drive one or more of the light emitting sources;
        each light emitting source configured to generate a light beam in response to a corresponding one of the one or more modulation signals, each light beam contributing to form a single optical signal; and
        the optical element configured to direct the light beams to exit the implantable optical transmitter device distributed in a pattern in which a peak position of light intensity of each light beam is separated from a corresponding peak position of light intensity of an adjacent light beam by at least a first distance and less than a second distance, wherein the implantable optical transmitter device is configured to be embedded within biological tissue and the first distance and the second distance are based on characteristics of the biological tissue; and
    an external optical receiver device-configured to detect light generated by the plural light emitting sources.

2. The system of claim 1 wherein the first distance is greater than 0.5 millimeters and the second distance is less than 50 millimeters.

3. The system of claim 1 wherein the optical element comprises at least one optical window.

4. The system of claim 3 wherein each at least one optical window comprises a lens, an anti-reflective coating, a diffusing layer, a micro-structured surface or any combination thereof.

5. The system of claim 3 wherein the plural light emitting sources comprise N light emitting sources and the at least one optical window comprises M optical windows, with N greater than or equal to M.

6. The system of claim 3 wherein the implantable optical transmitter device further comprises a ferrule having plural openings, the ferrule positioned at the proximal end of a housing and the at least one optical window recessed from the proximal end of the housing by at least a thickness of the ferrule.

7. The system of claim 6 wherein the plural light emitting sources comprise N light emitting sources and the plural openings comprise M openings, with N greater than or equal to M.

8. The system of claim 1 wherein each of the plural light emitting sources comprises any of a light emitting diode and a vertical-cavity surface-emitting laser.

9. The system of claim 1 wherein a first group of the plural light emitting sources comprises vertical-cavity surface-emitting lasers and a second group of the plural light emitting sources comprises light emitting diodes.

10. The system of claim 1 wherein the plural light emitting sources are configured to operate between 400 nm and 1400 nm.

11. The system of claim 1 wherein the plural light emitting sources are configured to operate between 600 nm and 1300 nm.

12. The system of claim 1 wherein the one or more drivers are configured to operate based on any of on-off keying modulation and multiple amplitude shift keying modulation.

13. A method for transcutaneous optical communication, the method comprising:
    at an implantable optical transmitter device:
        at one or more of plural light emitting sources, generating a light beam in response to a corresponding one or more modulation signals, each light beam contributing to form a single optical signal; and
        directing the light beams to exit the implantable optical transmitter device distributed in a pattern in which a peak position of light intensity of each light beam is separated from a corresponding peak position of light intensity of an adjacent light beam by at least a first distance and less than a second distance, wherein the implantable optical transmitter device is configured to be embedded within biological tissue and the first distance and the second distance are based on characteristics of the biological tissue.

14. The method of claim 13 further comprising:
    at an external optical receiver device positioned to detect one or more of the light beams:
        at one or more of plural photodiodes, detecting light generated by the plural light emitting sources and responsively generating an external detection signal;
        amplifying the external detection signal; and
        receiving the amplified detection signal and generating a reconstructed data signal.

15. The method of claim 13 wherein the first distance is greater than 0.5 millimeters and the second distance is less than 50 millimeters.

16. The method of claim 13 wherein the directing is by an optical element comprising at least one optical window.

17. The method of claim 13 wherein each of the plural light emitting sources comprises any of a light emitting diode and a vertical-cavity surface-emitting laser.

18. The method of claim 13 wherein a first group of the plural light emitting sources comprises vertical-cavity surface-emitting lasers and a second group of the plural light emitting sources comprises light emitting diodes.

19. The method of claim 13 wherein the generating a light beam in response to a corresponding one of the one or more modulation signals is based on on-off keying modulation or multiple amplitude shift keying modulation.

20. An implantable device comprising:
    one or more drivers, plural light emitting sources, and an optical element;
    each of the one or more drivers configured to convert a digital data signal into one or more modulation signals to drive one or more of the light emitting sources;
    each light emitting source configured to generate a light beam in response to a corresponding one of the one or more modulation signals, each light beam contributing to form a single optical signal; and
    the optical element configured to direct the light beams to exit the implantable device distributed in a pattern in which a peak position of light intensity of each light beam is separated from a corresponding peak position of light intensity of an adjacent light beam by at least a first distance and less than a second distance, wherein the device is configured to be embedded within biological tissue and the first distance and the second distance are based on characteristics of the biological tissue.

21. The implantable device of claim 20 wherein the first distance is greater than 0.5 millimeters and the second distance is less than 50 millimeters.

22. The implantable device of claim 20 wherein the optical element comprises plural optical windows.

23. The implantable device of claim 22 wherein each optical window of the plural optical windows comprises a lens, an anti-reflective coating, a diffusing layer, a micro-structured surface or any combination thereof.

24. The implantable device of claim 22 wherein the plural light emitting sources comprise N light emitting sources and the plural optical windows comprise M optical windows, with N greater than or equal to M.

25. The implantable device of claim 20 wherein the optical element comprises a single optical window.

26. The implantable device of claim 25 wherein the single optical window comprises a lens, an anti-reflective coating, a diffusing layer, a micro-structured surface or any combination thereof.

27. The implantable device of claim 25 further comprising a ferrule having plural openings, the ferrule positioned at a proximal end of a housing and the single optical window recessed from the proximal end of the housing by at least a thickness of the ferrule.

28. The implantable device of claim 27 wherein the plural light emitting sources comprise N light emitting sources and the plural openings comprise M openings, with N greater than or equal to M.

29. The implantable device of claim 27 wherein each of the plural light emitting sources comprises any of a light emitting diode and a vertical-cavity surface-emitting laser.

30. The implantable device of claim 27 wherein a first group of the plural light emitting sources comprises vertical-cavity surface-emitting lasers and a second group of the plural light emitting sources comprises light emitting diodes.

31. The implantable device of claim 27 wherein the plural light emitting sources are configured to operate between 400 nm and 1400 nm.

32. The implantable device of claim 27 wherein the plural light emitting sources are configured to operate between 600 nm and 1300 nm.

33. The implantable device of claim 27 wherein the one or more drivers are configured to operate based on on-off keying modulation or multiple amplitude shift keying modulation.

* * * * *